(12) United States Patent
Edquist et al.

(10) Patent No.: US 11,969,514 B2
(45) Date of Patent: Apr. 30, 2024

(54) SANITIZATION SYSTEMS AND METHODS WITH FAR-UVC

(71) Applicant: B/E AEROSPACE, INC., Winston Salem, NC (US)

(72) Inventors: John Edquist, Milwaukee, WI (US); Eric Johannessen, Holbrook, NY (US)

(73) Assignee: B/E AEROSPACE, INC., Winston Salem, NC (US)

( * ) Notice: Subject to any disclaimer, the term of this patent is extended or adjusted under 35 U.S.C. 154(b) by 339 days.

(21) Appl. No.: 17/194,976

(22) Filed: Mar. 8, 2021

(65) Prior Publication Data
US 2022/0226518 A1    Jul. 21, 2022

Related U.S. Application Data

(60) Provisional application No. 63/139,672, filed on Jan. 20, 2021.

(51) Int. Cl.
*A61L 2/10* (2006.01)
*A61L 2/24* (2006.01)

(52) U.S. Cl.
CPC ........ *A61L 2/10* (2013.01); *A61L 2/24* (2013.01); *A61L 2202/11* (2013.01); *A61L 2202/14* (2013.01); *A61L 2202/25* (2013.01)

(58) Field of Classification Search
CPC .... A61L 2/10; A61L 2202/11; A61L 2202/25; A61L 2/24; A61L 2202/14
See application file for complete search history.

(56) References Cited

U.S. PATENT DOCUMENTS

| | | | |
|---|---|---|---|
| 10,130,727 B1 * | 11/2018 | Byrnes | A61L 2/24 |
| 10,228,622 B2 * | 3/2019 | Kimsey-Lin | A61L 2/10 |
| 2014/0361703 A1 * | 12/2014 | Fornage | H05B 45/39 |
| | | | 315/205 |
| 2016/0089459 A1 | 3/2016 | Boodaghians et al. | |
| 2019/0030195 A1 * | 1/2019 | Hatti | A61L 2/24 |
| 2020/0230271 A1 * | 7/2020 | Choi | F21V 1/20 |

FOREIGN PATENT DOCUMENTS

| | | | | |
|---|---|---|---|---|
| EP | 2668964 | | 12/2013 | |
| WO | WO-2019068189 A1 * | | 4/2019 | A61L 2/10 |

OTHER PUBLICATIONS

European Patent Office, European Search Report dated Jun. 17, 2022 in Application No. 22152467.1.

* cited by examiner

*Primary Examiner* — Sean E Conley
*Assistant Examiner* — Justin Hwang
(74) *Attorney, Agent, or Firm* — SNELL & WILMER L.L.P.

(57) ABSTRACT

A sanitization system for an aircraft may comprise: a power source; and a plurality of sanitizers in electrical communication with the power source, each sanitizer in the plurality of sanitizers configured to emit ultraviolet radiation having an average wavelength between 200 and 230 nm, the power source configured to provide power to each sanitizer in the plurality of sanitizers in succession during an occupied flight of the aircraft.

9 Claims, 7 Drawing Sheets

SANITIZATION SYSTEMS AND METHODS WITH FAR-UVC

CROSS-REFERENCE TO RELATED APPLICATIONS

This application is a non-provisional of, and claims priority to, and the benefit of U.S. Provisional Application No. 63/139,672, entitled "AIRCRAFT PASSENGER SERVICE UNIT FAR-UV SANITIZATION SYSTEM," filed on Jan. 20, 2021, which is hereby incorporated by reference in its entirety.

FIELD

The present disclosure relates generally to sanitization systems and methods and, more particularly, to sanitization systems and method using FAR-UVC for aircrafts.

BACKGROUND

The recent novel-coronavirus (SARS-COV-2) outbreak has negatively impacted the safety and health of many people. Pathogens can be transmitted via direct airborne transmission between users or via indirect contact transmission from different users occupying the same space at different times. For example, lingering pathogens may remain on contact surfaces of an aircraft cabin to be spread to passengers and/or crew members on a subsequent flight. The safety of passengers and crew members may be improved by performing disinfecting treatments to surfaces, such as seats, ceiling/wall panels, handles, and lavatory surfaces, etc., to mitigate the presence of pathogens on such surfaces. However, conventional disinfection procedures between flights may take time and may thus adversely affect the operating efficiency of the aircraft (increased interval time between flights), and the effectiveness and quality of such conventional treatments are often difficult to verify/track.

SUMMARY

A sanitization system for an aircraft is disclosed herein. The sanitization system may comprise: a power source; and a plurality of sanitizers in electrical communication with the power source, each sanitizer in the plurality of sanitizers configured to emit ultraviolet radiation having an average wavelength between 200 and 230 nm, the power source configured to provide power to each sanitizer in the plurality of sanitizers in succession during an occupied flight of the aircraft.

In various embodiments, the sanitization system may further comprise a plurality of lights in electrical communication with the power source. The sanitization system may further comprise a passenger service unit, the passenger service unit including a light in the plurality of lights and a first sanitizer in the plurality of sanitizers. The passenger service unit may comprise an energy storage device in electrical communication with the power source and the first sanitizer. The energy storage device may be configured to charge during operation of the sanitization system. The energy storage device may be configured to power the first sanitizer. The sanitization system may further comprise a controller in operable communication with the plurality of sanitizers, the controller may be operable to: activate, via a processor, the first sanitizer in the plurality of sanitizers; receive, via the processor, a radiation dosage corresponding to the first sanitizer; compare, via the processor, the radiation dosage to a threshold dosage; and deactivate, via the processor, the first sanitizer in response to the radiation dosage meeting or exceeding the threshold dosage. The controller may further be operable to: activate, via the processor, a second sanitizer in the plurality of sanitizers in response to deactivating the first sanitizer. The sanitization system may further comprise a plurality of the energy storage device including the energy storage device, each energy storage device being electrically coupled to a corresponding sanitizer in the plurality of sanitizers. The power source may be configured to charge the plurality of the energy storage device simultaneously during operation of the sanitizer. The plurality of sanitizers may include at least one of an excimer lamp and a light emitting diode (LED).

A method is disclosed herein. The method comprises: activating, via a processor, a first sanitizer in response to an occupied flight cycle for an aircraft being determined, the first sanitizer configured to emit ultraviolet radiation having an average wavelength between 200 and 230 nm; deactivating, via the processor, the first sanitizer; and subsequently; activating, via the processor, a second sanitizer in response to deactivating the first sanitizer.

In various embodiments, the method may further comprise deactivating, via the processor, the first sanitizer in response to a dosage of the ultraviolet radiation from the first sanitizer exceeding a threshold dosage. The method may further comprise: receiving, via the processor, the dosage of the ultraviolet radiation from the first sanitizer; and comparing, via the processor, the dosage from the first sanitizer to the threshold dosage. The method may further comprise: receiving, via the processor, an indication that a row in a cabin of the aircraft has a desired cleaning event; and requesting, via the processor, an energy status of an energy storage device, the energy storage device in electrical communication with a third sanitization device disposed proximate the row in the cabin. The method may further comprise: receiving, via the processor, the energy status; and activating, via the processor, the third sanitization device via power from the energy storage device in response to the energy status being charged.

A control system for a sanitization system of an aircraft is disclosed herein. The control system may comprise: a power source; a main controller in operable communication with a plurality of local controllers, each local controller in operable communication with a sanitizer, a light, and an energy storage device in a respective row of a cabin of the aircraft, each sanitizer in a plurality of sanitizers configured to emit ultraviolet radiation having an average wavelength between 200 and 230, the main controller configured to: command the power source to power the plurality of sanitizers in succession, and command the power source to charge a plurality of energy storage devices simultaneously with powering the plurality of sanitizers in succession.

In various embodiments, the control system may further comprise a plurality of sensors, each sensor in operable communication with a respective local controller in the plurality of local controllers. Each sensor in the plurality of sensors may be configured to detect an occupancy within the row of the cabin of the aircraft. Each sanitizer in the plurality of sanitizers may comprise at least one of an excimer lamp and a light emitting diode (LED).

The forgoing features and elements may be combined in various combinations without exclusivity, unless expressly indicated herein otherwise. These features and elements as well as the operation of the disclosed embodiments will become more apparent in light of the following description and accompanying drawings.

BRIEF DESCRIPTION OF THE DRAWINGS

The subject matter of the present disclosure is particularly pointed out and distinctly claimed in the concluding portion of the specification. A more complete understanding of the present disclosure, however, may best be obtained by referring to the following detailed description and claims in connection with the following drawings. While the drawings illustrate various embodiments employing the principles described herein, the drawings do not limit the scope of the claims.

DETAILED DESCRIPTION

The following detailed description of various embodiments herein makes reference to the accompanying drawings, which show various embodiments by way of illustration. While these various embodiments are described in sufficient detail to enable those skilled in the art to practice the disclosure, it should be understood that other embodiments may be realized and that changes may be made without departing from the scope of the disclosure. Thus, the detailed description herein is presented for purposes of illustration only and not of limitation. Furthermore, any reference to singular includes plural embodiments, and any reference to more than one component or step may include a singular embodiment or step. Also, any reference to attached, fixed, connected, or the like may include permanent, removable, temporary, partial, full or any other possible attachment option. Additionally, any reference to without contact (or similar phrases) may also include reduced contact or minimal contact. It should also be understood that unless specifically stated otherwise, references to "a," "an" or "the" may include one or more than one and that reference to an item in the singular may also include the item in the plural. Further, all ranges may include upper and lower values and all ranges and ratio limits disclosed herein may be combined.

In various embodiments, Far-UV (222 nm wavelength light) has promise to work in occupied spaces but may utilize significant power to disinfect an entirety of a cabin. Additionally, Far-UV (222 nm wavelength light) may have limitations as to total dosage a human may receive. In various embodiments, integrating Far-UV (222 nm wavelength light) via excimer lamps into each passenger service unit for each aircraft row with intelligent operations may minimize total power of a sanitization system, internal power storage, tracking passenger exposure, and/or adjust dosages based on contemporary pathogens. In various embodiments, a central controller may be embedded in a flight attendant panel to track flight data, automate functions of the sanitization system, and/or enable manual control by a cabin crew.

In various embodiments, the sanitization system disclosed herein, may enable a Far-UV (222 nm wavelength light) excimer lamp to actively disinfect surfaces during flight in a safe manner while balancing power restrictions and/or exposure guidance. In various embodiments, smart features may allow the sanitization system to perform context oriented functionality all built into the flight attendant panel.

Figure 1:
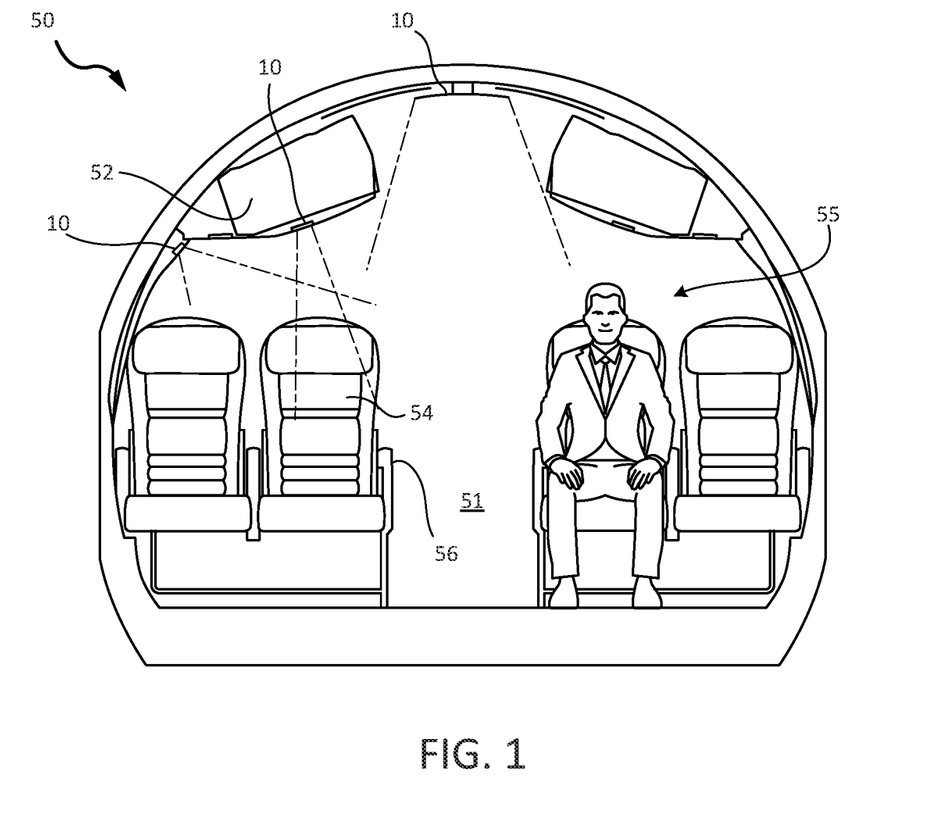
FIG. 1 illustrates a view of a cabin of an aircraft, in accordance with various embodiments.

With reference to FIG. 1, a cabin 51 of an aircraft 50 is shown, according to various embodiments. The aircraft 50 may be any aircraft such as an airplane, a helicopter, or any other aircraft. The aircraft 50 may include various lighting systems 10 that emit visible light to the cabin 51. Pathogens, such as viruses and bacteria, may remain on surfaces of the cabin 51, and these remaining pathogens may result in indirect contact transmission to other people (e.g., subsequent passengers). For example, the cabin 51 may include overhead bins 52, passenger seats 54 for supporting passengers 55, handles 56, lavatory surfaces, and other structures/ surfaces upon which active pathogens may temporarily reside. As will be discussed further below, in order to reduce the transmission/transfer of pathogens between passengers, one or more of the lighting systems 10 may blend disinfecting electromagnetic radiation output into the visible light in order to facilitate disinfection of the cabin 51 (e.g., during flights and/or between flights). The lighting systems 10 may be broken down into different addressable lighting regions that could be used on an aircraft. For example, the regions on an aircraft may include sidewall lighting, cross-bin lighting, over wing exit lighting, ceiling lighting, direct lighting, flex lights, reading lights, dome lights, lavatory lights, mirror lights, cockpit lights, cargo lights, etc. The regional breakdown of the lighting system allows lighting control over broad areas of the aircraft. In various embodiments, lighting system 10 may be disposed in/incorporated by a passenger service unit (PSU) for a row of seats. As such, a lighting system 10 could be provided for each row of an aircraft, as well as for each section of different sections of a given row of an aircraft.

Figure 2:
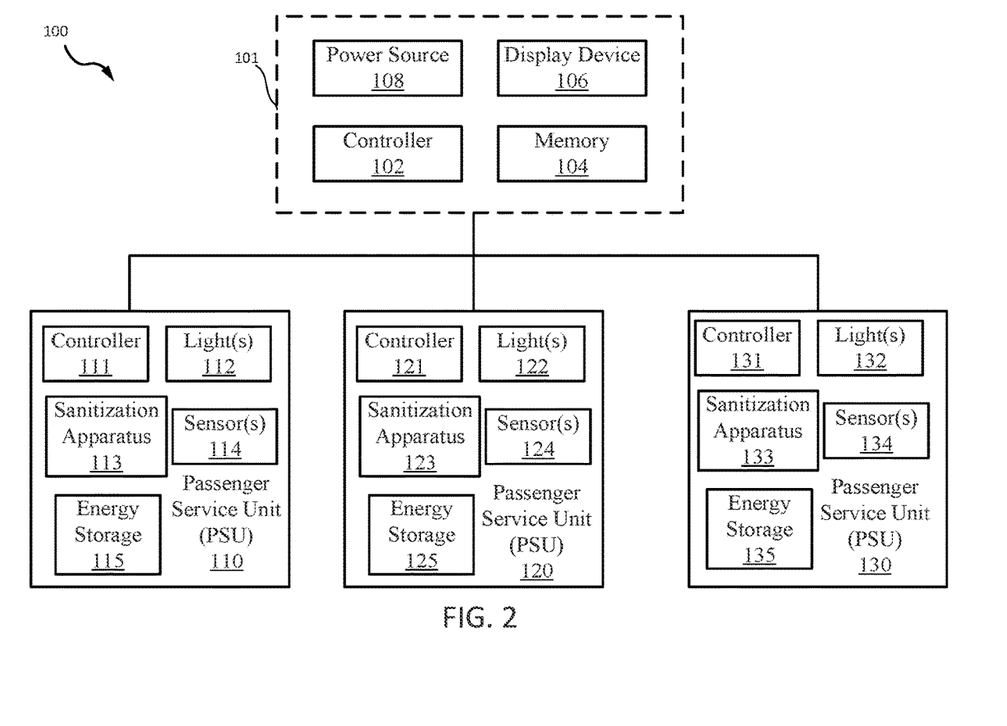
FIG. 2 illustrates a schematic view of a sanitization system, in accordance with various embodiments.

Referring now to FIG. 2 a schematic view of a sanitization system 100 for an aircraft cabin, is illustrated, in accordance with various embodiments. In various embodiments, the sanitization system 100 comprises a main control system 101 and a plurality of PSUs (e.g., first PSU 110, second PSU 120, third PSU 130, etc.). Although illustrated as including three PSUs, the number of PSUs of a sanitization system 100 is not limited in this regard. For example, a PSU may be disposed in each row of seats disposed in a respective column of an aircraft cabin. For example, a cabin with 50 rows and 3 columns may have 150 PSUs (e.g., each row in each column having a PSU). In various embodiments, the PSUs are not limited to rows in the aircraft cabin and may be placed throughout the aircraft cabin as well. For example, PSUs, in accordance with the present disclosure, may be disposed in the lavatory, aisles, cockpit, or any other area of an aircraft cabin where it may be desirable to have sanitization.

In various embodiments, the main control system 101 includes a controller 102 and a memory 104 (e.g., a database or any appropriate data structure; hereafter "memory 104" also may be referred to as "database 104"). The controller 102 may include one or more logic devices such as one or more of a central processing unit (CPU), an accelerated processing unit (APU), a digital signal processor (DSP), a field programmable gate array (FPGA), an application specific integrated circuit (ASIC), or the like (e.g., controller 102 may utilize one or more processors of any appropriate type/configuration, may utilize any appropriate processing architecture, or both). In various embodiments, the controller 102 may further include any non-transitory memory known in the art. The memory 104 may store instructions usable by the logic device to perform operations. Any appropriate computer-readable type/configuration may be utilized as the memory 104, any appropriate data storage architecture may be utilized by the memory 104, or both.

The database 104 may be integral to the control system 101 or may be located remote from the control system 101. The controller 102 may communicate with the database 104 via any wired or wireless protocol. In that regard, the controller 102 may access data stored in the database 104. In various embodiments, the controller 102 may be integrated into computer systems onboard an aircraft. Furthermore, any number of conventional techniques for electronics configuration, signal processing and/or control, data processing and the like may be employed. Also, the processes, functions, and instructions may can include software routines in conjunction with processors, etc.

System program instructions and/or controller instructions may be loaded onto a non-transitory, tangible computer-readable medium having instructions stored thereon that, in response to execution by the processor, cause the controller 102 to perform various operations. The term "non-transitory" is to be understood to remove only propagating transitory signals per se from the claim scope and does not relinquish rights to all standard computer-readable media that are not only propagating transitory signals per se. Stated another way, the meaning of the term "non-transitory computer-readable medium" and "non-transitory computer-readable storage medium" should be construed to exclude only those types of transitory computer-readable media which were found in In Re Nuijten to fall outside the scope of patentable subject matter under 35 U.S.C. § 101.

The instructions stored on the memory 104 of the controller 102 may be configured to perform various operations. The schematic flow chart diagram of FIG. 3 includes a controller method 300 that the processor of the controller 102 may perform, in accordance with various embodiments. Generally, the controller 102 is operably (e.g., electrically or wirelessly through a network) coupled to the plurality of PSUs (e.g., PSUs 110, 120, 130).

In various embodiments, the main control system 101 from FIG. 2 further comprises a power source 108 and a display device 106. The power source 108 may comprise any power source known in the art, such as a battery, or the like. In various embodiments, the display device 106 may be configured to provide inputs into the control system 101 and alternate between various modes (e.g., alternating from an in-flight mode to a post-flight mode, as described further herein). In various embodiments, the sanitization system 100 may alternate modes automatically in response to detecting a change in mode is desired, as described further herein.

In various embodiments, the main control system 101 is in operable communication with each PSU in the plurality of PSUs (e.g., PSUs 110, 120, 130). In various embodiments, each PSU comprises a local controller (e.g., controllers 111, 121, 131). Each local controller (e.g., controllers 111, 121, 131) may be in accordance with main controller 102). For example, each local controller (e.g., controllers 111, 121, 131) may include one or more logic devices such as one or more of a central processing unit (CPU), an accelerated processing unit (APU), a digital signal processor (DSP), a field programmable gate array (FPGA), an application specific integrated circuit (ASIC), or the like (e.g., controllers 111, 121, 131 may utilize one or more processors of any appropriate type/configuration, may utilize any appropriate processing architecture, or both). In various embodiments, the controllers 111, 121, 131 may each further include any non-transitory memory known in the art. The memory may store instructions usable by the logic device to perform operations. Any appropriate computer-readable type/configuration may be utilized as the memory, any appropriate data storage architecture may be utilized by the memory, or both.

In various embodiments, each PSU (e.g., PSUs 110, 120, 130) may comprise light(s) (e.g., light(s) 112, 122, 132), a sanitizer (e.g., sanitizer 113, 123, 133), sensor(s) (e.g., sensors 114, 124, 134), and a local energy storage device (e.g., energy storage 115, 125, 135). As described further herein, the controller 102 may command the various local controllers (e.g., controllers 111, 121, 131) to instruct the devices therein. In various embodiments, the local energy storage device (e.g., energy storage 115, 125, 135) may comprise any electrical storage device, such as a capacitor, a supercapacitor, a superconducting magnetic storage, or the like.

In various embodiments, the power source 108 is sized and configured to power all of the lights (e.g., light(s) 112, 122, 132, etc.) of all of the PSUs (e.g., PSUs 110, 120, 130, etc.) of a sanitization system 100. Since at least some of the lights of each PSU are generally activated by a passenger, and passenger's often leave the lights off in flight, additional power may be available in power source 108 during flight. Thus, excess power from a power source 108 of reading lights for PSUs in an aircraft cabin (e.g., aircraft cabin 51 from FIG. 1, may be utilized to power sanitization system 100 as described further herein.

In various embodiments, each sanitizer (e.g., sanitizers 113, 123, 133) may comprise excimer lamp(s), light emitting diodes (LEDs), or the like. Each sanitizer disclosed herein (e.g., sanitizers. 113, 123, 133) is configured to emit FAR-UV radiation. "FAR-UV" radiation, as disclosed herein, refers to radiation with average wavelengths between 200 and 230 nms. In various embodiments, the average wavelengths of FAR-UV radiation may be approximately 222 nm. In various embodiments, FAR-UV radiation may be safe for human exposure/consumption up to a certain dosage level. In this regard, use of FAR-UV radiation in the sanitization system 100 may permit sanitization of an aircraft cabin (e.g., cabin 51 from FIG. 1) while passengers are occupying the respective cabin.

In various embodiments, each sanitizer (e.g., sanitizers 113, 123, 133) may be connected via digital communications, discrete communications, or wireless communications to a respective local controller (e.g., controllers 111, 121, 131). In various embodiments, a respective local controller may be configured to monitor a health of a respective sanitizer, as well as a life of a respective sanitizer. For example, controller 111 may be configured to receive excimer lamp life data from the sanitizer 113, as well as energy storage charge data from energy storage 115. In various embodiments, each PSU (e.g., PSUs 110, 120, 130) may be configured to track a total dosage of FAR-UV supplied to a given area. For example, the controller 111 of PSU 110 may receive a duration that sanitizer 113 has been in operation and limit operation when a threshold dosage is being approached.

In various embodiments there may be a single sensor or a plurality of sensors for each PSU. For example, sensor(s) (e.g., sensor(s) 114, 124, 134) may each include a microphone array, an occupancy sensor, a manual trigger, or a combination thereof. In this regard, the sanitization system 100 may be configured to detect occupancy and/or configured to detect an event where cleaning may be desired, such as a detecting a sneeze, a cough, or the like.

Figure 3:
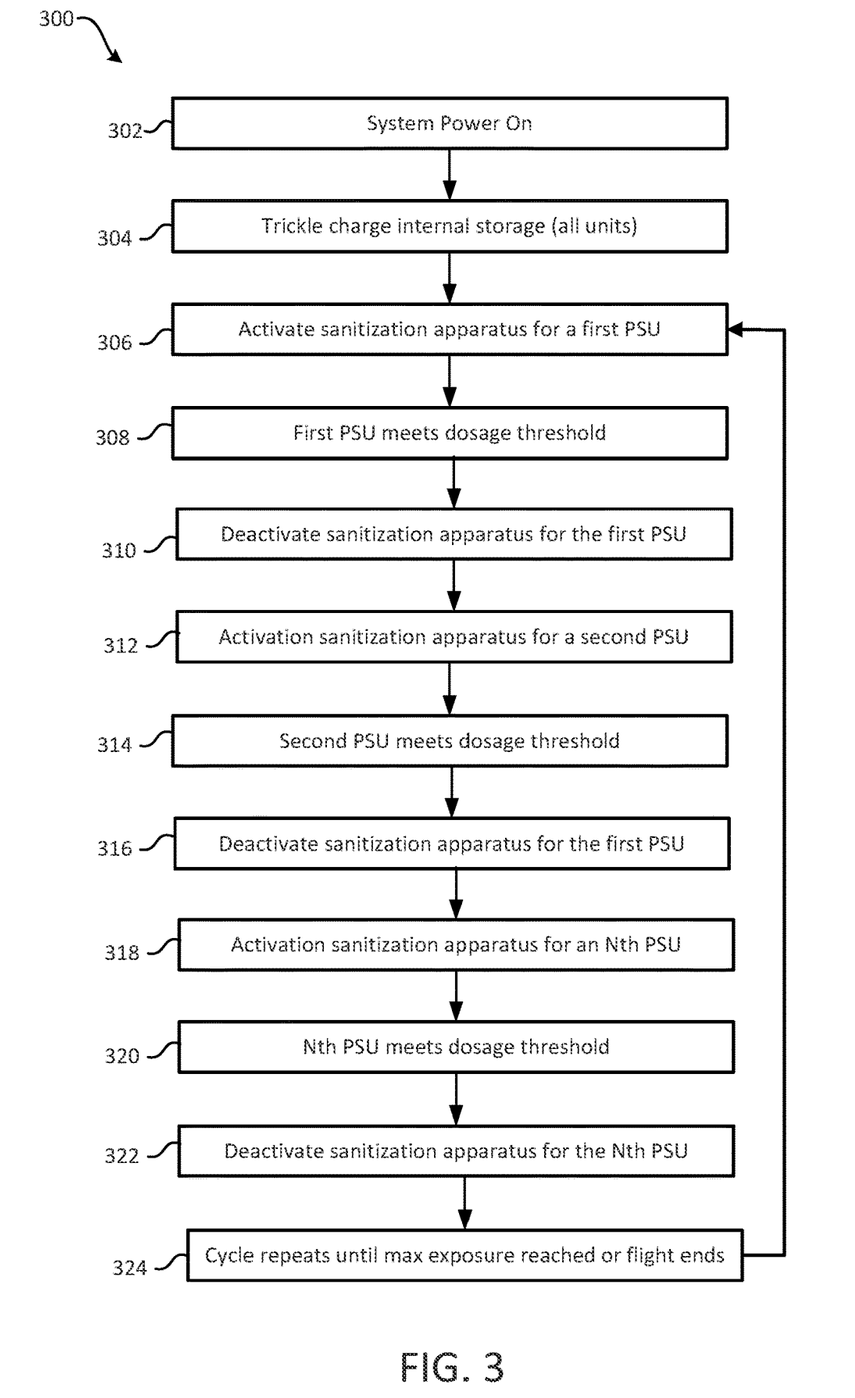
FIG. 3 is process performed by a control system for a sanitization system, in accordance with various embodiments.

Referring now to FIG. 3, a process for in-flight operation of the main control system 101 from FIG. 2 is illustrated, in accordance with various embodiments. In various embodiments, the process 300 includes powering on the system (step 302). Powering on the system may be a command from a display device (e.g., display device 106 from FIG. 2 by a user), or in response to a main controller receiving any indication that a flight cycle has started (e.g., an indication gas-turbine engines have been powered on, an indication the aircraft has started moving, or the like).

In various embodiments, the process 300 may further include trickle charging internal storage for all PSUs (step 304). For example, with brief reference to FIG. 2, the power source 108 may be commanded, via main controller 102, to trickle charge internal storage in each PSU (i.e., first energy storage device 115, second energy storage device 125, all the way to an Nth energy storage device 135). In this regard, each local internal storage for a respective PSU may be charged during a typical flight cycle and provide a backup capacity, or a surge capacity, in the event the power source 108 does not have enough power to continue operation of sanitization system 100.

In various embodiments, the process 300 further comprises sanitizing each row in an aircraft cabin (e.g., cabin 51 from FIG. 1) in succession (steps 308-322). In this regard, power consumption may be greatly reduced compared to sanitizing all rows simultaneously. In various embodiments, the sanitizer of a first PSU (e.g., first PSU 110 from FIG. 2) is activated (step 306), tracked until a dosage threshold is met (step 308), and deactivated in response to the dosage threshold is met (step 310). In various embodiments, the dosage threshold may be configurable based on guidance or the like to prevent excess exposure to individuals of a respective row in an aircraft cabin (e.g., cabin 51 from FIG. 1).

In various embodiments, in response to the first PSU being deactivated in step 310 a second sanitizer of a second PSU (e.g., second PSU 120 from FIG. 2) is activated (step 312), tracked until the dosage threshold is met (step 314), and deactivated in response to the dosage threshold being met (step 316). This process may be repeated for each row in an aircraft cabin (e.g., cabin 51) as described previously herein, until all rows have been sanitized. For example, a first sanitization cycle may end with an Nth PSU (e.g, Nth PSU 130 from FIG. 2) in an Nth row of an aircraft cabin (e.g., cabin 51 from FIG. 1), where N is the total number of rows in the cabin. In this regard, in response to the N−1 row's sanitizer being deactivated, the Nth PSU (e.g., Nth PSU 130 from FIG. 2) is activated (step 318), tracked until the dosage threshold is met (step 320), and deactivated in response to the dosage threshold being met (step 322). In various embodiments, a "row" as described herein may include any number of seats and have at least one seat that abuts an aisle in an aircraft cabin.

In various embodiments, the sanitization cycle (i.e., steps 306-322) may be repeated until a total dosage threshold is met or a flight cycle ends (step 324). In this regard, for longer flights, steps 306-322 may be repeated multiple times throughout a flight. In various embodiments, only a single sanitization cycle (i.e., steps 306-322) may be performed for a given flight. In various embodiments, an exposure threshold may be predetermined based on guidance to prevent excess exposure to individuals and may be customizable for various sanitization systems 100 from FIG. 2.

In various embodiments, the main controller 102 from the main control system 101 in FIG. 2 may be configured to perform process 300. For example, the main controller 102 may be configured to receive through local controllers, dosage data corresponding to a total duration of exposure during a flight cycle for a respective sanitizer, compare the dosage data to a threshold dosage, commanding the respective sanitizer to deactivate in response to meeting the threshold dosage, and activate the next sanitizer in response to deactivating the previous sanitizer (e.g., steps 306-312).

Figure 4:
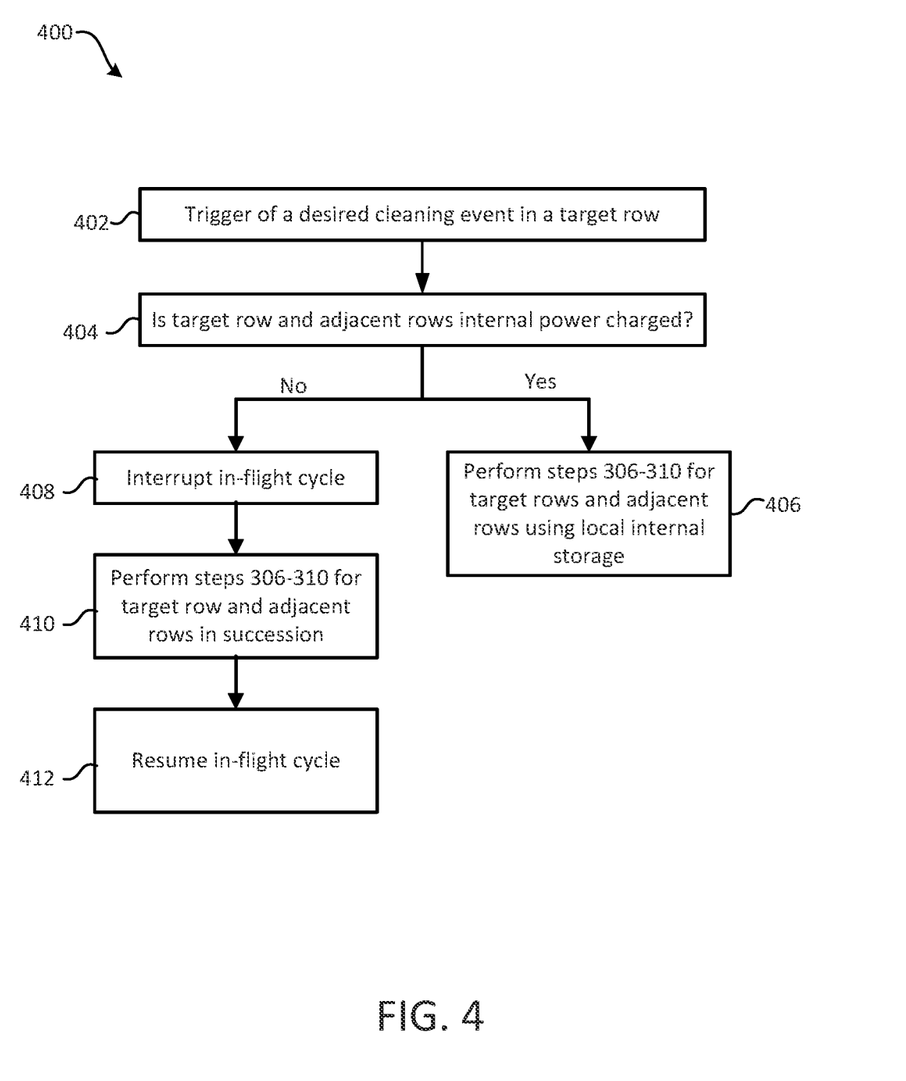
FIG. 4 is a process performed by a control system for a sanitization system, in accordance with various embodiments.

Referring now to FIG. 4, a process 400 of sanitization system 100 from FIG. 2 for handling a surge capacity for power source 108 from FIG. 2 is illustrated, in accordance with various embodiments. In various embodiments, the surge capacity process may be triggered manually by a user (e.g., a flight attendant), or triggered automatically (e.g., in response to a sensor detecting a desired cleaning event from a sneeze a cough, or the like).

In various embodiments, the process 400 comprises a trigger of a desired cleaning event in a target row (step 402). In various embodiments, the trigger may be input manually to the main controller 102 of the control system 101 from FIG. 2 through the display device 108. In various embodiments, the trigger may be activated automatically in response to the main controller 102 from FIG. 2 receiving an indication that a cleaning event is desired in a respective target row. For example, a sensor (e.g., sensor 114 from FIG. 1) may detect a sneeze and send a signal to the local controller (e.g., controller 111) that a sneeze was detected. In various embodiments, the local controller (e.g., controller 111) may send a signal to the main controller 102 that the sneeze was detected in the respective row (e.g., a first row with the first PSU 110).

In various embodiments, in response to the desired cleaning event in the target row being determined, the main controller 102 of the control system 101 from FIG. 2 may determine whether the target row and the adjacent rows internal power (e.g., energy storage 115, 125, and/or 135) are charged). For example, the main controller 102 may command a respective local controller (e.g., controller 111) to provide a charge status of the respective energy storage (e.g., energy storage 115) for each row to be sanitized due to the desired cleaning event. In this regard, if each row to be cleaned due to the desired cleaning event has a charged internal power, the energy storage for the respective row may be used to sanitize the respective rows, while the typical in-flight sanitization cycle (e.g., process 300 from FIG. 3) is maintained (step 406). However, if the main controller 102 receives an indication that the target row and adjacent rows internal power is not charged, the in-flight cycle (e.g., process 300) may be interrupted (step 408), and the power from power source 108 in FIG. 2 may be utilized to perform steps 306-310 for the target row and adjacent rows (step 410). In various embodiments, when power source 108 is supplying the power, the sanitization steps may be performed in succession (i.e., in series), in accordance with process 300 from FIG. 3. In this regard, the target row may be sanitized first, followed by a first adjacent row, followed by a second adjacent row, etc. In this regard, real time power consumption of the power source 108 from FIG. 1 may be reduced to allow use of lights within each PSU (e.g., light(s) 112, 122, 132, etc.).

In various embodiments, once the target rows and the adjacent rows are sanitized in step 410, the in-flight sanitization cycle may resume (step 412).

Figure 5:
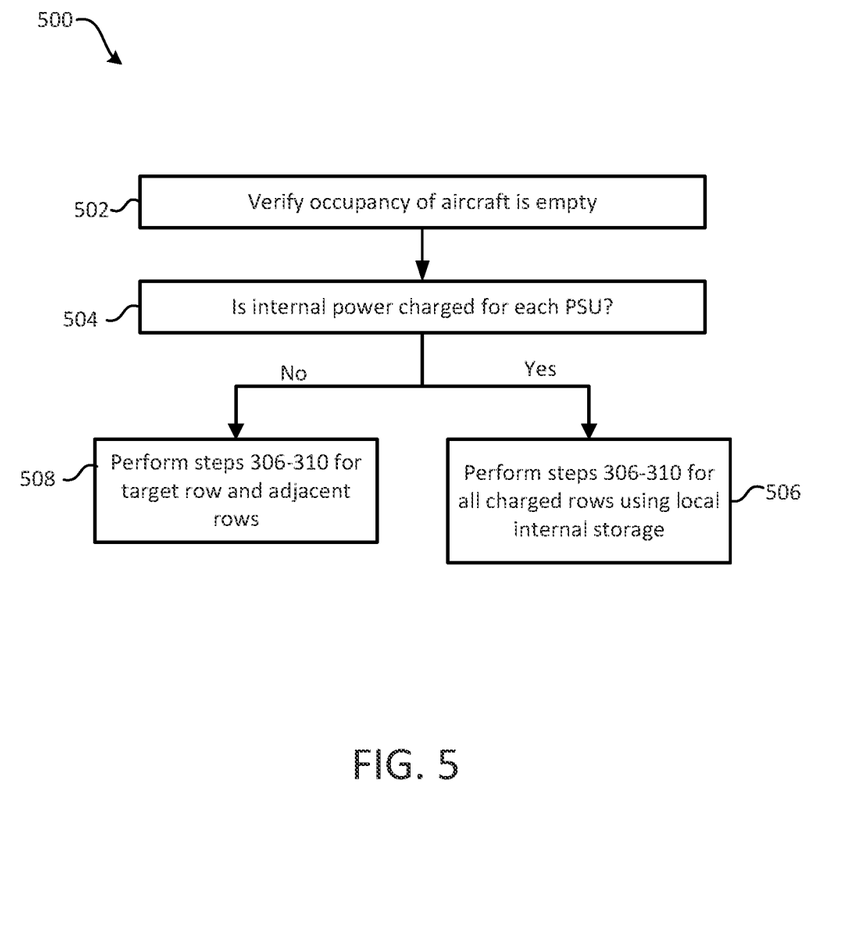
FIG. 5 is a process performed by a control system for a sanitization system, in accordance with various embodiments.

Referring now to FIG. 5, a process 500 for post-flight operation of the main control system 101 from FIG. 2 is illustrated, in accordance with various embodiments. In various embodiments, the process 500 includes verifying occupancy of an aircraft cabin (e.g., cabin 51 from FIG. 1) is empty. In this regard, the main controller 102 of control system 101 from FIG. 1 may request an indication from each PSU in the cabin whether an individual is detected by a sensor (e.g., sensor(s) 114, 124, 134, etc.) from FIG. 2. Each local controller (e.g., controllers 111, 121, 131) may request an occupancy status from a respective sensor (e.g., sensor(s) 114, 124, 134) and relay the occupancy status to the main controller 102. In response to determining the cabin 51 from FIG. 1 is empty, the sanitization system 100 from FIG. 1 may determine which local power storage (e.g., energy storage 115, 125, 135, etc.) of each PSU in a plurality of PSUs (e.g., PSUs 110, 120, 130) are charged (step 504). In this regard, the charged energy storage devices may be used to power the sanitization steps 306-310 for their respective PSUs simultaneously with all other charged energy storage devices (step 506), while steps 306-310 may be performed sequentially, in accordance with process 300, using the power source 108 from FIG. 2 for the PSUs with the un-charged or partially charged energy storage devices. In this regard, a first row with a first un-charged PSU may be sanitized first, followed by a second row with a second un-charged PSU, etc.

Figure 6:
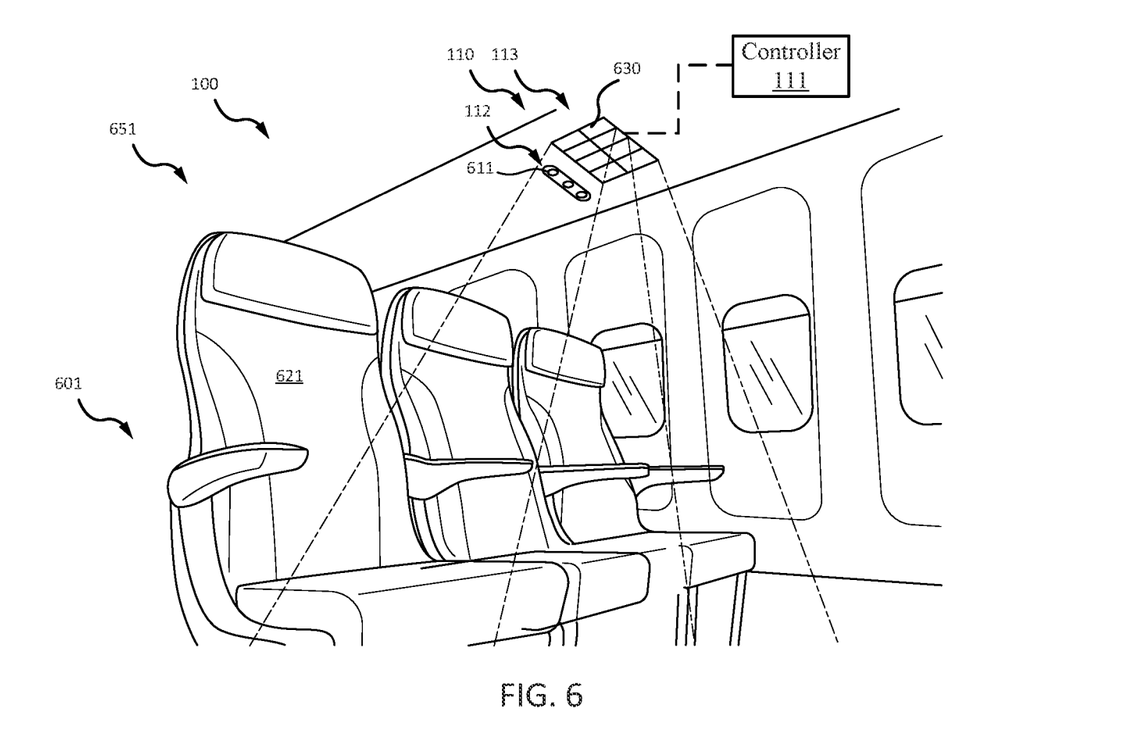
FIG. 6 is a perspective view of a portion of a sanitization system 100, in accordance with various embodiments.

Referring now to FIG. 6, a perspective view of a portion of the sanitization system 100 from FIG. 2 is illustrated, in accordance with various embodiments. The sanitization system 100 includes the light(s) 112 and the sanitizer 113. In various embodiments, each light light(s) 112 may correspond to a seat in a respective row. For example, a first light 611 may be configured to align towards a first seat 621 in a row 601 of in the aircraft cabin 651. In this regard, each light in the light(s) 112 in a PSU 110 may be configured to emit light towards a seat in a row of the respective PSU 110.

In various embodiments, the sanitizer 113 in a PSU 110 includes an excimer lamp 630. Although illustrated as including a plurality of the excimer lamp 630, any number of excimer lamps 630 are within the scope of this disclosure. In various embodiments, the local controller 111 may adjust a beam direction of a respective excimer lamp 630 during a sanitization process (e.g., process 300, process 400, and/or process 500). In various embodiments, the sanitization system 100 may be configured to direct the light away from a passenger's head (e.g., towards the tray tables, or the like).

Figure 7:
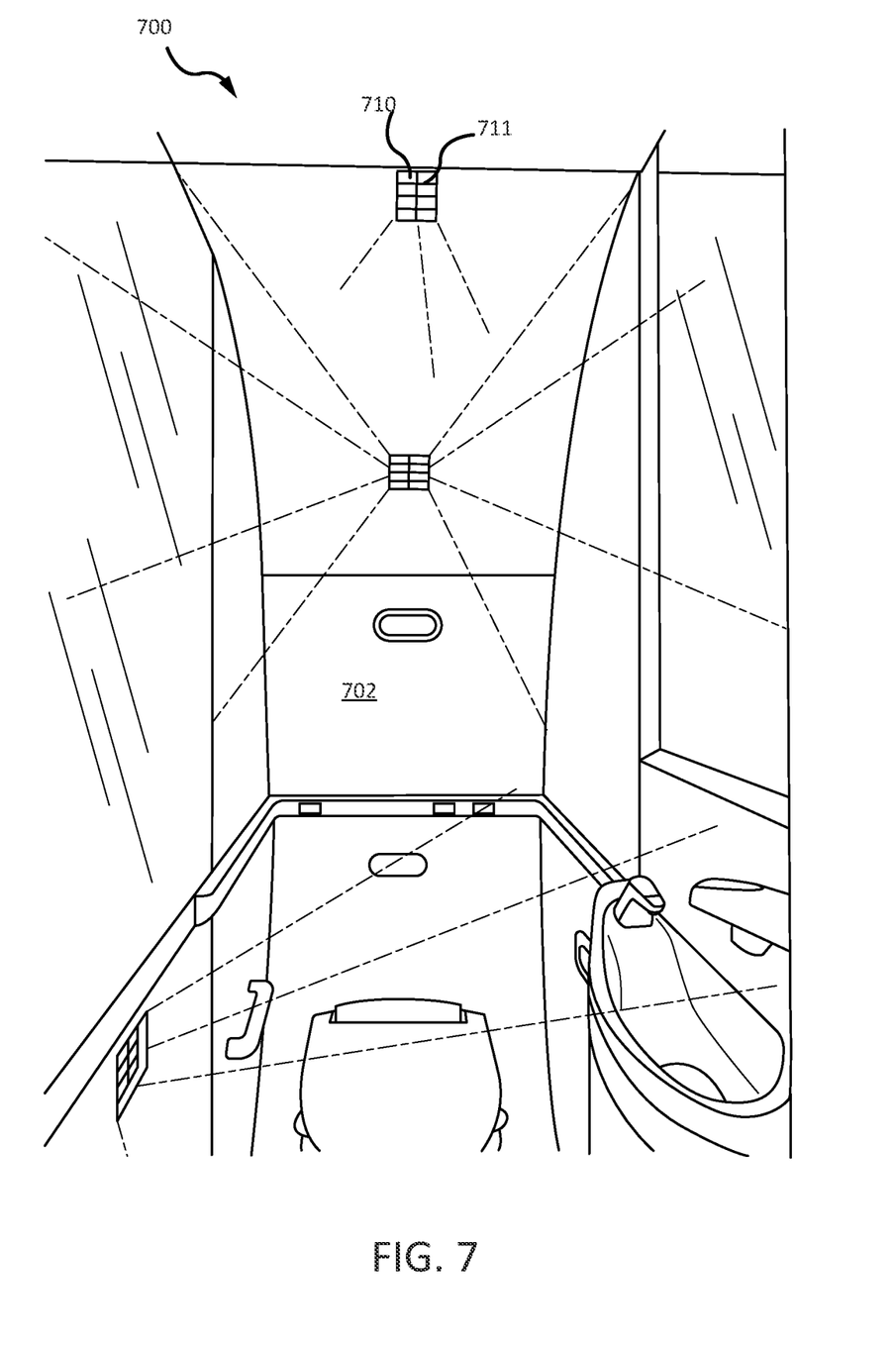
FIG. 7 is a perspective view of a lavatory in an aircraft, in accordance with various embodiments.

Referring now to FIG. 7, a perspective view of a sanitization system 700 is illustrated, in accordance with various embodiments. In various embodiments, the sanitization system 700 may be disposed in a lavatory 702 of an aircraft cabin (e.g., aircraft cabin 51 from FIG. 1). In this regard, the sanitization system 700 may be configured in a manner similar to sanitization system 100. For example, the sanitization system may include sensor(s) configured to detect whether the bathroom is occupied (e.g., sensor(s) 114 from FIG. 2), a sanitizer 710 (e.g., an excimer lamp 711, or an LED), a local energy storage system (e.g., energy storage 115 from FIG. 2), and a controller (e.g., controller 111 from FIG. 1). In various embodiments, the sanitization system 700 may be in communication with main controller 102 from the sanitization system 100 from FIG. 2. In this regard, the lavatory 702 may be configured to be sanitized during in-flight cycle of process 300 (e.g., sequentially between rows, at a beginning of the cycle, at an end of the cycle, or the like). In various embodiments, the lavatory 702 may be configured to be sanitized after use (e.g., in response to detecting a user entering and detecting a user leaving).

Benefits, other advantages, and solutions to problems have been described herein with regard to specific embodiments. Furthermore, the connecting lines shown in the various figures contained herein are intended to represent exemplary functional relationships and/or physical couplings between the various elements. It should be noted that many alternative or additional functional relationships or physical connections may be present in a practical system. However, the benefits, advantages, solutions to problems, and any elements that may cause any benefit, advantage, or solution to occur or become more pronounced are not to be construed as critical, required, or essential features or elements of the disclosure. The scope of the disclosure is accordingly to be limited by nothing other than the appended claims, in which reference to an element in the singular is not intended to mean "one and only one" unless explicitly so stated, but rather "one or more." Moreover, where a phrase similar to "at least one of A, B, or C" is used in the claims, it is intended that the phrase be interpreted to mean that A alone may be present in an embodiment, B alone may be present in an embodiment, C alone may be present in an embodiment, or that any combination of the elements A, B and C may be present in a single embodiment; for example, A and B, A and C, B and C, or A and B and C. Different cross-hatching is used throughout the figures to denote different parts but not necessarily to denote the same or different materials.

Systems, methods and apparatus are provided herein. In the detailed description herein, references to "one embodiment," "an embodiment," "various embodiments," etc., indicate that the embodiment described may include a particular feature, structure, or characteristic, but every embodiment may not necessarily include the particular feature, structure, or characteristic. Moreover, such phrases are not necessarily referring to the same embodiment. Further, when a particular feature, structure, or characteristic is described in connection with an embodiment, it is submitted that it is within the knowledge of one skilled in the art to affect such feature, structure, or characteristic in connection with other embodiments whether or not explicitly described. After reading the description, it will be apparent to one skilled in the relevant art(s) how to implement the disclosure in alternative embodiments.

Furthermore, no element, component, or method step in the present disclosure is intended to be dedicated to the public regardless of whether the element, component, or method step is explicitly recited in the claims. No claim element herein is to be construed under the provisions of 35 U.S.C. 112(f) unless the element is expressly recited using the phrase "means for." As used herein, the terms "comprises," "comprising," or any other variation thereof, are intended to cover a non-exclusive inclusion, such that a process, method, article, or apparatus that comprises a list of elements does not include only those elements but may include other elements not expressly listed or inherent to such process, method, article, or apparatus.

Finally, it should be understood that any of the above described concepts can be used alone or in combination with any or all of the other above described concepts. Although various embodiments have been disclosed and described, one of ordinary skill in this art would recognize that certain modifications would come within the scope of this disclosure. Accordingly, the description is not intended to be exhaustive or to limit the principles described or illustrated herein to any precise form. Many modifications and variations are possible in light of the above teaching.

What is claimed is:

1. A sanitization system for an aircraft, the sanitization system comprising:
a power source; and
a plurality of passenger service units, each of the plurality of passenger service units comprising:
a sanitizer in electrical communication with the power source, the sanitizer configured to emit ultraviolet radiation having an average wavelength between 200 and 230 nm, the power source configured to provide power to the sanitizer of a first passenger service unit and subsequently to the sanitizer of a second passenger service unit during an occupied flight of the aircraft; and
an energy storage device in electrical communication with the power source and the sanitizer, the energy storage device configured to charge during the occupied flight; and
a controller in operable communication with the sanitizer of each of the plurality of passenger service units, the controller configured to:
command the power source to provide power to the sanitizer of each of the plurality of passenger service units in a successive order during the occupied flight of the aircraft;
command the power source to trickle charge the energy storage device of each of the plurality of passenger service units simultaneously with powering each of the plurality of the sanitizer in the successive order;
verify an occupancy of the aircraft is empty after the occupied flight, and
in response to determining the energy storage device of each of the plurality of passenger service units is charged, commanding the energy storage device of each of the plurality of passenger service units to power all of the sanitizer from the plurality of passenger service units simultaneously.

2. The sanitization system of claim 1, further comprising a plurality of lights in electrical communication with the power source.

3. The sanitization system of claim 1, wherein the controller is further operable to:
activate, via a processor, a first sanitizer in a plurality of the sanitizer;
receive, via the processor, a radiation dosage corresponding to the first sanitizer detected by a sensor;
compare, via the processor, the radiation dosage to a threshold dosage; and
deactivate, via the processor, the first sanitizer in response to the radiation dosage meeting or exceeding the threshold dosage.

4. The sanitization system of claim 3, wherein the controller is further operable to:
activate, via the processor, a second sanitizer in the plurality of the sanitizer in response to deactivating the first sanitizer.

5. The sanitization system of claim 1, wherein the sanitizer includes at least one of an excimer lamp and a light emitting diode (LED).

6. A control system for a sanitization system of an aircraft, the control system comprising:
a power source;
a plurality of local controllers;
a main controller in operable communication with the plurality of local controllers, each local controller in operable communication with a sanitizer, a light, and an energy storage device in a respective row of a cabin of the aircraft, the sanitizer configured to emit ultraviolet radiation having an average wavelength between 200 and 230, the main controller configured to:
operate in an in-flight mode during a flight cycle of the aircraft, the in-flight mode including:
command the power source to power each of a plurality of the sanitizer in a successive order,
command the power source to trickle charge each of a plurality of the energy storage device simultaneously with powering each of the plurality of the sanitizer in succession; and
operate in a post-flight mode after the flight cycle, the post-flight mode including:
verify an occupancy of the aircraft is empty, and
in response to determining the energy storage device associated with each of in the plurality of the sanitizer is charged, commanding each of the plurality of the energy storage device to power a respective sanitizer in the plurality of the sanitizer to power all of the plurality of the sanitizer simultaneously.

7. The control system of claim 6, further comprising a plurality of sensors, each sensor in operable communication with a respective local controller in the plurality of local controllers.

8. The control system of claim 7, wherein each of the plurality of sensors is configured to detect the occupancy within the row of the cabin of the aircraft.

9. The control system of claim 7, wherein the sanitizer comprises at least one of an excimer lamp and a light emitting diode (LED).

* * * * *